United States Patent [19]
Sen

[11] Patent Number: 5,284,932
[45] Date of Patent: Feb. 8, 1994

[54] PROCESS FOR PURIFYING AND CHARACTERIZING MYOTROPHIA, A NOVEL PEPTIDE THAT REGULATES MYOCARDIAL GROWTH

[75] Inventor: Shubha Sen, Solon, Ohio

[73] Assignee: The Cleveland Clinic Foundation, Cleveland, Ohio

[21] Appl. No.: 578,935

[22] Filed: Sep. 7, 1990

[51] Int. Cl.$^5$ .............................................. C07K 7/00
[52] U.S. Cl. ................................... 530/324; 530/325; 530/326; 530/329; 530/330
[58] Field of Search ......................................... 530/300

[56] References Cited
PUBLICATIONS

Sen et al., *J. Biol Chem.*, vol. 265(27), 1990, pp. 16635–16643.
Trezise et al., *Proc. Natl. Acad. Sci USA*, vol. 86, 1989, pp. 5454–5458.
Heden et al., *FEBS Lett.*, vol. 194, 1986, pp. 327–332.

*Primary Examiner*—Ronald W. Griffin
*Assistant Examiner*—Pamela S. Webber
*Attorney, Agent, or Firm*—Fay, Sharpe, Beall, Fagan, Minnich & McKee

[57] ABSTRACT

The present invention is directed to a process for purifying and characterizing "myotrophin", a novel soluble protein factor that is believed to regulate myocardial hypertrophy in hypertension. In addition, the invention is directed to the purified and partially characterized protein factor produced by the process of the present invention, as well as uses of this factor, or its antagonist to control cardiac hypertrophy.

1 Claim, 12 Drawing Sheets

PROCESS FOR PURIFYING AND CHARACTERIZING MYOTROPHIA, A NOVEL PEPTIDE THAT REGULATES MYOCARDIAL GROWTH

BACKGROUND OF THE INVENTION

The present invention is directed to a process for purifying and characterizing a novel soluble protein factor, designated "myotrophin" by the inventors, that is believed to influence cardiac hypertrophy associated with hypertension. In addition, the invention is directed to the purified and partially characterized myotrophin produced by the process of the present invention, as well as the use of this factor and/or its antagonist to regulate myocardial growth.

Hypertrophy is generally defined as the increase in size of an organ or structure independent of natural growth that does not involve tumor formation. Hypertrophy of an organ or tissue is due either to an increase in the mass of the individual cells (true hypertrophy) such as in the hypertrophy of a muscle produced by physical exercise, or to an increase in the number of cells making up the tissue (hyperplasia) or to both. Certain organs, such as the heart, consist of cells which lack the ability to divide, and in such cases, hypertrophy results in an increase in the size rather than in the number of constituent cells. In other tissues such as the liver, hypertrophy of the organ is effected principally by an increase in the number of cells.

Cardiac hypertrophy relates to the enlargement of the heart due to the increased size of the myocardium, or more particularly, to the increased size of the myocyte cells which make up the myocardium layer of the heart. The myocardium is the middle layer of the walls of the heart composed of cardiac muscle. The increase in size of the heart may be due to physiological, as well as pathological, stimuli. For example, the size of the heart may be increased as a result of long periods of physical exercise or because of a valvular disorder or other types of pathological disorders.

As a result of the increased stress and/or strain placed upon the heart in condition of hypertension due to the increased total peripheral resistance, etc., cardiac hypertrophy has long been associated with hypertension.

However, the lack of a close parallelism between blood pressure levels and degree of cardiac hypertrophy has been demonstrated both in clinical studies as well as in experimental animal models (Grant, R. D., *Am. Heart J.* 46, pp. 154–158, 1953; Ehrstrom, M. C. *Acta Med. Scand.* 103, pp. 86–93, 1948; Sen, S., Tarazi, R. C., Khairallah, P. A., and Bumpus, F. M., *Cir. Res.* 35, pp. 775–781, 1974; and, Sen, S., Tarazi, R. C., Bumpus, F. M., *Cardiovas. Res.* 10, pp. 254–261, 1976). Thus, factors other than blood pressure controls appear to exist that play a role in altering myocardial structure, reducing compliance and diminishing performance and thus determining the hemodynamic state throughout course of hypertension.

Moreover, while studies performed by the inventors and others (Sen, S., Tarazi, R. C., Khairallah, P. A., and Bumpus, F. M., (abstract) *Clin. ExD. Pharmacol. Physiol.* 3, pp. 173–177, 1976; Sen, S., and Bumpus, F. M., *Am. J. Cardiol.* 44, pp. 954–958, 1979; Sen, S., Tarazi, R. C., and Bumpus, F. M., *Am. J. Physiol.* 240, pp. H408–H412, 1981; Sen, S., Tarazi, R. C., and Bumpus, F. M., *Hypertension* 2, pp. 169–176, 1980; Yamori, Y., Mori, C., Nishio, T., Ooshima, et al., *Am. J. Cardiol.* 44, pp. 964–969, 1969; Hollander, W., Madoff, I., Paddock, J., and Kirkpatrick, B., *Circ. Res. (Suppl.* 6) 38, pp. 63–72, 1976; Freis, E., *Spontaneous Hypertension: Pathogenesis and Complications* (Okamoto, K., ed.), pp. 231–244, Springer-Verlag, N.Y., 1972; and, Tomanek, R., Davis, J., and Anderson, S. C., *Cardiovasc. Res.* 13, pp. 173–182, 1979) have confirmed that cardiac hypertrophy in spontaneously hypertensive rats (SHR) can be prevented or reversed to some degree by antihypertensive treatment, such treatment is highly variable depending on the specific antihypertensive agent utilized, etc.

Of significance is the marked diversity in the ability of various antihypertensive drugs to reverse cardiac hypertrophy, even though all these drugs reduced arterial pressure to the same degree. For example, the inventors have shown (Sen, S., Tarazi, R. C., Khairallah, P. A., and Bumpus, F. M., *Cir. Res.* 35, pp. 775–781, 1974; and, Sen, S., Tarazi, R. C., and Bumpus, F. M., *Cardiovasc. Res.* 11, pp. 427–433, 1977) that alpha-methyldopa lowered pressure and reduced cardiac weight to normal levels. However, hydralazine controlled pressure, but did not reverse hypertrophy, whereas minoxidil normalized blood pressure, but actually increased heart weight (Sen, S., Tarazi, R. C., Khairallah, P. A., and Bumpus, F. M., *Cir. Res.* 35, pp. 775–781, 1974; and, Sen, S., Tarazi, R. C., and Bumpus, F. M., *Cardiovasc. Res.* 11, pp. 427–433, 1977). These differences among various drugs could be related to: (a) varied hemodynamic effects; (b) differences in the reflexes in sympathetic stimulation; or (c) direct biochemical alteration of cardiac muscle.

In a more recent study (Sen, S., Tarazi, R. C., *Am. J. Physiol.* 244, pp. H97–H101, 1983), the inventors have shown that a combination of a beta blocker and a vasodilator, which led to moderate blood pressure control without increased myocardial catecholamine content, reversed myocardial hypertrophy, whereas reduction of either blood pressure alone or myocardial catecholamines alone failed to regress hypertrophy. These observations suggest involvement of the beta adrenergic system in modulation of myocardial hypertrophy. However, it is not known how the adrenergic system may modify the protein structure of the myocardium. It is possible that increased wall stress, which is induced by adrenergic stimulation, triggers increased protein synthesis; an hypothesis supported by the observation that increased stress produces fundamental alteration in the contractility of the heart (Albert, N. R., Mulleri, L. A., and Litten, R. Z., *Am. J. Cardiol.* 114, 947–953, 1979).

As a result, while reversal of cardiac hypertrophy with proper antihypertensive therapy has been proven, it has been shown by the present inventors and others that regression of hypertrophy is highly variable depending upon the specific hypertensive agent utilized. In addition, the biochemical aspect of such reversal is still relatively unknown. Thus, the mechanisms of the development or regression of myocardial hypertrophy cannot be fully explained by blood pressure control alone.

What is clear, however, is that the development of hypertrophy is initiated by a variety of myocardial stimuli, either mechanical or humoral. It is likely that the myocardium, in turn, produces a chemical signal that is then responsible for triggering protein synthesis and myocardial cell growth.

In a recent study, the inventors demonstrated the existence of a factor in the hypertrophied myocardium of spontaneously hypertensive rats (SHR) that stimulates protein synthesis in cultured adult rat myocytes in vitro (Sen, S., and Petscher C., *Hypertension* 9, pp. 261-266, 1987). In this study, the inventors described the partial purification of the stimulating factor with HPLC, first by using gel filtration and then DEAE columns. During successive purification attempts of the factor by an exchange chromatograph, the stimulating activity of the partially purified factor was only moderately increased. The molecular weight of the partially purified stimulating factor was tentatively estimated to be 8500 by a HPLC molecular sieve exclusion technique. In addition, trypsin digestion (pH 7.0-7.5) destroyed the stimulating activity. The data set forth in that study suggested that the stimulating factor is of a protein moiety, however, additional research was clearly necessary in order to purify and characterize the soluble factor and to determine its physiological importance.

The present invention is directed to the isolation and purification of this protein factor to homogeneity, and to the partially elucidation of its internal amino acid sequence. From a homology search using three different databases, the isolated, purified, and partially characterized protein factor appears to be a novel molecule with no identical homology with any known protein. The isolated, purified, and partially characterized protein factor has been named "myotrophin" by the present inventors.

SUMMARY OF THE INVENTION

In one aspect, the present invention is directed to a process for purifying myotrophin to homogeneity comprising a unique multi-step purification process involving ammonium sulphate precipitation, ion exchange chromatography using mono-Q columns at various pHs and reverse phase chromatography. In addition, the present invention relates to the myotrophin purified to homogeneity by the process of the present invention.

In a further aspect, the invention is directed to a process for determining the partial amino acid sequence of myotrophin by reducing, carboxymethylating, and digesting the purified myotrophin with trypsin. The digested material is then separated by reverse phase HPLC and sequenced. The partial amino acid sequences of myotrophin determined by the process of the present inventors are also included in the invention.

In an additional aspect, the present invention is directed to the use of myotrophin and/or its antagonist to regulate myocardial hypertrophy.

DESCRIPTION OF THE DRAWINGS

The following is a brief description of the drawings which are presented for the purpose of illustrating the invention and not for the purpose of limiting same.

FIG. 3A shows UV and FIG. 3B indicates biological activities as shown by % stimulation of $^3$H leucine into neonatal myocyte protein. CN=buffer control. The A and D fractions were pooled to assay for biological activity.

FIG. 4A: UV absorption of 280 nm.

FIG. 4B: biological stimulator's activity by neonatal cell assay.

FIG. 5A: UV absorption at 280 nm.

FIG. 5B: biological activity by neonatal cell assay.

FIG. 6A: UV absorption at 214 nm.

FIG. 6B: stimulator's activity by neonatal cell assay.

FIG. 7A: UV absorbance at 214 nm where myotrophin emerged as a single peak.

FIG. 7B: corresponding biological activity of "B". CN =control buffer; B =myotrophin's stimulator activity. Data expressed as % stimulation over control for four separate sets of experiments (mean SEM). The results indicate that insulin (0.5 $\mu$g), when added, showed significant stimulation.

DETAILED DESCRIPTION OF THE INVENTION

Figure 1:
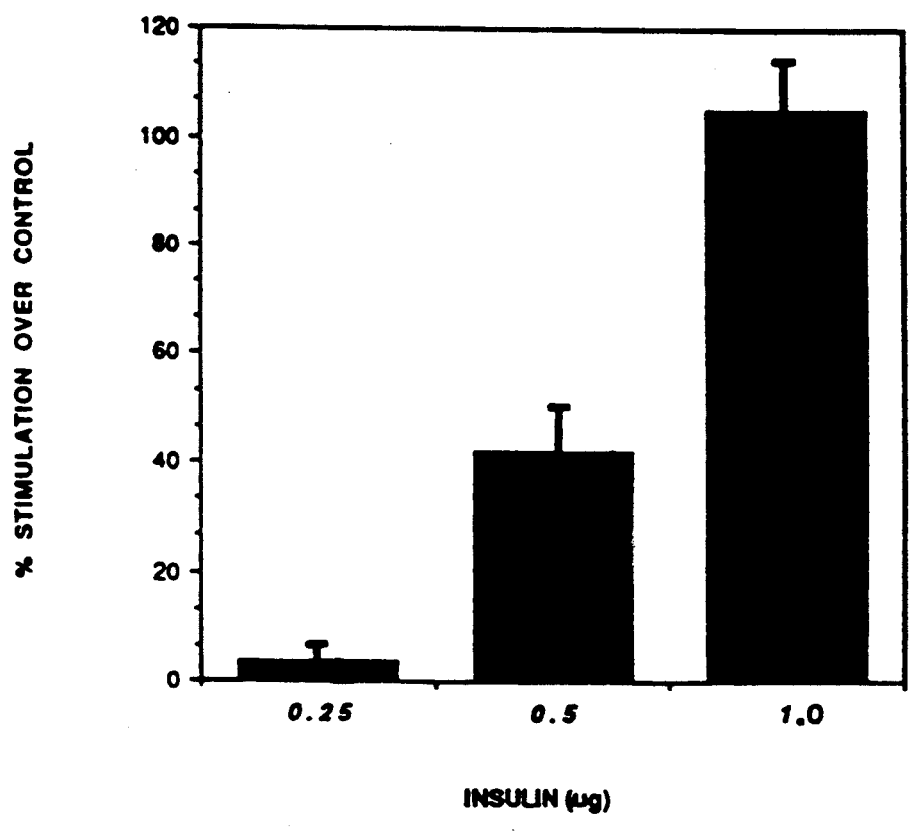
FIG. 1 is a graph demonstrating the effect of insulin on the incorporation of $^3$H leucine into myocyte protein (DPH/$\mu$g DNA). Data are expressed as % stimulation over control. The data indicates that insulin increased incorporation in a dose-dependent manner.

The present invention is directed to a process for purifying and characterizing "myotrophin", a novel soluble protein factor that is now believed to regulate myocardial hypertrophy in hypertension. In addition, the invention is directed to the purified and partially characterized protein factor produced by the process of the present invention, as well as uses of this factor, or its antagonist, to control cardiac hypertrophy.

More particularly, the inventors have isolated and purified a soluble factor (designated "myotrophin") which is thought to trigger the protein synthesis which results in the increase of muscle mass associated with myocardial hypertrophy. Using the stimulation of protein synthesis in isolated cardiac myocytes obtained from normal rat hearts as an assay system, the present inventors have identified a soluble molecule (i.e. myotrophin) from the hypertrophied myocardium of spontaneously hypertensive rats (SHR). This molecule, when purified to homogeneity, appears to be a novel peptide with a molecular weight of about 12,000 daltons.

Furthermore, in addition to the purification of the stimulating factor, and the demonstration of myotrophin's homogeneity, the present inventors have partially elucidated its structure. Specifically, the sequence of six internally liberated peptides containing 5-26 residues have been determined. From a homology search using three different data bases, the determined amino acid of the six internally liberated peptides indicates that myotrophin appears to be a novel molecule with no identical homology with any known protein and/or previously described growth factor.

Moreover, the inventors have further demonstrated that through the incorporation of radio-labeled amino acids, such as $^{14}C$ phenylalanine or $^{3}H$ leucine, into myocyte proteins in both neonatal and adult myocardial cells, that the myotrophin stimulating factor produces significant physiological effects, such as an increase in cell size and accelerated myofibrol growth in a dose-dependent manner.

Specifically, it has been found that myotrophin causes a dose-dependent increase in the surface area and appearance of organized myofibrils of neonatal cardiac myocytes, which is apparent within 48 hours. When myotrophin was added to other cells, it did not demonstrate any measurable effect on fibroblast, endothelial cell, or aortic smooth muscle cell size.

Moreover, it was found that myotrophin is present in human, dog, and rat hypertrophied hearts (52% stimulation of protein synthesis over control) and only in small amounts in normal hearts (5-6% stimulation). Thus, myotrophin appears to be specific for cardiac myocytes since it is not present in and does not stimulate protein synthesis in cultured endothelial cells, smooth muscle cells, or fibroblasts.

These discoveries indicate that the myotrophin factor is involved in the initiation of cardiac hypertrophy and plays a significant role in both the control and regression of hypertrophy associated with hypertension and unrelated to blood pressure control alone. Furthermore, as a result of this discovery, appropriate antagonists can be developed as therapeutic agents for inhibiting myocardial hypertrophy and/or hypertension.

The following example illustrates the specific embodiments of the present invention:

MATERIALS

All SHR were obtained from Taconic Farm (Germantown, N.Y.). Timed pregnant rats were obtained from Hilltop Farm, Scottdale, Pa. All chemicals and solvents used in this study were ACS certified analytical reagents and HPLC grade. Media and other reagents for tissue culture, including fetal bovine serum albumin, fetuine, transferrin, hydrocortisone, and insulin were purchased from Sigma Chemical Co. (St. Louis, Mo.). Collagenase Type II and TLCK-treated Trypsin were purchased from Worthington Biochemical (Freehold, N.J.). $^{3}H$-Leucine and $^{14}C$ Phenylalanine were purchased from Amersham Corporation (Chicago, Ill.).

METHODS

Cardiac Myocyte Bioassay System

The inventors used a two-part bioassay system to define the effect of the putative factor and to follow its activity during purification. The system included both neonatal and an adult myocyte cultures. Maintaining adult myocytes in culture, in sufficient numbers to perform a routine assay for a long time period, is a difficult task. However, the neonatal cells can be maintained in culture for at least five days without a problem, and a large number of cells can be cultured without difficulty. Furthermore, the response of adult and neonatal cells for growth or stimulatory factors may be different. In this example, the inventors used neonatal cells in culture for daily routine assay, and adult myocytes were used to confirm the stimulatory activity of the active fractions only.

A. Neonatal Cell Assay System

The neonatal cells were isolated and were cultured as described by Claycomb (Claycomb, W. C., *Exp. Cell Res.* 131, pp. 231-236, 1980). Briefly, ventricles from the hearts of three day old rat pups were harvested and suspended in a small amount of Joklik's media. The tissue was minced and incubated in the presence of collagenase for 20 minutes (84 units/ml; Worthington Biochemicals, Freedhold, N.J., USA) in a water bath at 37° C. The released detached cells were aspirated with a pipette and transferred into a 50 ml tube. The residual tissue was redigested several times until all the cells were detached. The cells were suspended in DVF 12 media containing 5% (w/v) fetal bovine serum albumin. The cells were plated in a density of $2 \times 10^6/35$ mm well. The plates were kept in an incubator at 37° C. in a 95% $O_2$/5% $CO_2$ atmosphere. On the second day, the media were removed, and fresh medium added that was supplemented with fetuine (10 mg/ml), 2.5 ml transferrin (1 mg/ml) and 50 µl hydrocortisone. On the third day, the media was removed, and fresh medium added without fetuine, transferrin and hydrocortisone. $^{14}C$ Phenylalanine or $^{3}H$ leucine was added to each well and the cells incubated in the presence or absence of the factor myotrophin for two hours at 37° C. At the end of the incubation period, the medium was removed by aspiration, and 1 ml of SDS (0.1%)/NaOH (1N) solution was added. After the cells were allowed to stand for thirty minutes, with occasional shaking, 1 ml of bovine serum albumin (0.5 mg/ml) was added. One ml of 20% trichloro acetic acid (TCA) was added to each well. All the plates were kept in a cold room at 4° C. for thirty minutes. The proteins from each cell were collected into individual filter paper in a cell harvester (Brandel, Gaithersburg, Md.), and 5% TCA was used to wash them exhaustively until they were free of radioactive count. They were air dried for two hours and counted in a Beckman Beta Scintillation counter. Data are expressed as DPM/µg DNA. Insulin in a quantity of 0.5 units/ml was used as an external standard for daily assay.

B. Adult Myocytes Maintained in Culture

The adult myocytes were isolated and maintained in culture by following the method of Bugaisky and Zak (Bugaisky, L. B. and Zak, R., Circ. Res. 64, pp. 493-500, 1989). Hearts were removed from 17- to 20-week old SHR normal rats after decapitation, and the aortas cannulated and perfused with saline. They were then perfused with saline containing collagenase (200 units/ml Worthington Chemicals) for the first ten minutes without calcium, and then the next twenty minutes with 0.15 mM calcium. The heart tissue was minced and incubated in 10 cc of fresh collagenase in phosphate buffer for twenty minutes, and detached cells were harvested. The procedure was repeated four times, and the residual tissue was found to be negligible. The harvested cells were centrifuged at 500 rpm for one minute. The viability (rod shape) of the cells at this stage was only 50%. The viable cells were then purified by resuspending the cells in Medium 199 at a density of $5 \times 50^4/35$ mm, enriching them with 0.2% BSA, and keeping them at 37° C. for three hours (humidified and equilibrated with 5% $CO_2$ incubated at 37° C.). At the end of three hours, the viable cells settled at the bottom, and the supernatant was discarded with the dead cells. The viable cells were resuspended in Medium 199. At this time, the viability was between 80-90%. To maintain the cells in long term culture, the cells were made to adhere to a substrate, laminine. One ml of cell suspension was poured to well-coated laminine (0.1 ml lamanine/mg/100 ml Medium 199 solution over 35 mm surface area) and kept in an incubator for 24 hours at 37° C. Approximately 45% of the cells adhere to the substrate. The viability and the integrity of the cells were defined by examination under a phase contrast microscope, which can view a three dimensional structure.

For myotrophin assay, the adult myocytes in culture were incubated with $^{14}C$ phenylalanine and an aliquot of myotrophin or buffer for two hours at 37° C. The reaction was stopped by cooling at 0° C., the supernatant was removed, and the cells were washed four times with Medium 199. One ml of 0.1 N NaOH was added to lyse the cells, and a known aliquot (25 $\mu$l) was removed for determination of DNA. To the rest, 10% TCA was added to precipitate the protein, and the mixture was kept overnight at 4° C. The protein was filtered and collected using a cell harvester and counted after addition of scintillation fluid in a $\beta$ counter. Data are expressed as DPM/ng DNA. Insulin was used (0.5 $\mu$g) as an external daily standard.

C. Purification of Myotrophin

Rat ventricles were obtained from the heart of 14- to 16-week old spontaneously hypertensive rats (SHR) (Taconic Farms, Germantown, N.Y., USA). The hearts were cannulated through the aorta and were perfused with cold saline to remove blood, and ventricles were excised. All purification procedures were performed at 4° C. unless otherwise specified. The ventricles were homogenized in 7 vol of 50 mM sodium phosphate buffer, pH 7.4, containing 0.15 M NaCl and a mixture of 1 mM each of p-methanesulfonyl fluoride, N-ethylmaleiimide, EDTA, and 0.1 mM pepstatin in a Waring blender at the top speed for 30 s ($2 \times$). The homogenate was centrifuged at 10,000 $\times$g for thirty minutes and the supernatant was collected. The pellet was rehomogenized in 3 vol of the same buffer and was centrifuged in the same manner. The supernatant was collected and combined with the first extract. To the combined supernatant, 561 g/l, $(NH_4)_2SO_4$ was added by slowly adding solid $(NH_4)_2SO_4$ with constant stirring. The mixture was stirred for an additional thirty minutes. The protein precipitate was collected by centrifugation at 10,000$\times$g for ten minutes. The precipitate was dissolved in 200 ml of 20 mM Tris-HCl buffer, pH 7.6, and then dialyzed first against water for two hours and finally exhaustively against the same buffer (20 mM Tris-HCl). The dialyzed sample was centrifuged at 50,000 $\times$g for forty minutes, and the supernatant was collected.

The supernatant, in a volume of about 280 ml, was applied to Sephadex G-75 column ($5 \times 80$ cm), which was pre-equilibrated with 20 mM Tris-HCl buffer, pH 7.6. The column was eluted with the same buffer (FIG. 3). The fractions (55 through 70) containing the activity to stimulate $^3H$ leucine incorporation into protein were pooled. The combined fraction was then applied to a Pharmacia FPLC (fast protein, peptide, and polynucleotide chromatography) Mono-Q (HR 5/5) column, which was equilibrated with the same buffer. The column was eluted with a gradient of NaCl from 0 to 0.3 M, in 20 mM Tris-HCl buffer, pH 7.6, in a total gradient volume of 30 ml at a flow rate of 0.1 ml/min (FIG. 4). The active fractions (18 through 21) were pooled. The buffer in the pooled fraction changed to 20 mM L-histidine buffer, pH 5.6, by gel filtration on a Bio-Rad desalting column (Econo Pac 10 DG). The fraction was chromatographed on a Pharmacial Mono-Q (CHR5/5) column in 20 mM L-histidine buffer, pH 5.6. Elution was carried out with a gradient of NaCl from 0 to 0.2 M in a total volume of 20 ml at the flow rate of 1 ml/min. (FIG. 5). The fractions (15 and 16) that contained the activity were then pooled. The material was further purified by reverse phase HPLC on a Vydac $C_{18}$ column (0.46$\times$25 cm) using a linear acetonitrile gradient from 10% to 80% in 0.1% trifluoroacetic acid in water over a period of 70 minutes at a flow rate of ml/min. The UV-absorbance was monitored at 214 nm (FIG. 6). The fractions pooled as indicated by the horizontal mark were pooled and lyophilized. For bioassay, the dried material was dissolved in phosphate-buffered saline by intermittent mixing over a period of 120 minutes.

D. Characterization of Myotrophin

Amino acid sequence analysis was carried out using an Applied Biosystem model 470A protein sequencer attached with an on-line PTH analyzer. Direct Edman degradation of intact myotrophin did not yield detectable PTH amino acids, indicating that the $NH_2$ terminus is blocked. In order to obtain internal sequence of myotrophin, the pure myotrophin protein was reduced, carboxymethylated, and then digested with trysin according to the procedure set forth below. The digested material was separated by reverse phase HPLC on a Vydac $C_{18}$ a column, and the tryptic peptides obtained were sequenced.

Tryptic cleavage: Purified myotrophin (9 $\mu$g) was reduced with 1 mM dithiothreitol in 50 $\mu$l of 6N guanidine-HCl containing 50 mM Tris-HCl buffer, pH 8.5, for one hour, and then carboxymethylated with 1.05 mM iodoacetic acid. 0.5 $\mu$g of trypsin was added after dilution of the mixture by ten fold with 50 mM Tris-HCl, pH 8.0. After one hour, 0.5 $\mu$g of trypsin was added for the second time and incubated for an additional hour. Digestion was stopped by acidification by adding acetic acid to a final concentration of 5%. The digest was chromatographed directly on a Vydac $C_{18}$ column (Separations Groups, 0.46×25 cm) in 0.1% trifluoroacetic acid using a linear gradient of acetonitrile from 10% to 80% over a period of 70 minutes at the flow rate of 1 ml/min. Fractions were collected manually.

SDS-Polyacrylamide Gel Electrophoresis: SDS-polyacrylamide gel electrophoresis was performed at pH 8.0 using 8% to 25% gradient gel in Pharmacia phast system according to the manufacturer's protocol. The molecular weight of myotrophin was estimated using a protein standard kit from Sigma consisting of gels that were stained using silver stain.

E. Determination of DNA

DNA was determined by following the Fluorometric method of Labarca and Paigen (Labarca, C., and Paigen, K., *Anal. Biochem.* 102, pp. 344-352, 1980). The standard curve was prepared using Calf Thymas DNA. Bisbenzimide solutions (Hoechst 33258) was used as fluorescence dye and excitation at 356 nm was read in a Perkin Elmer LS-5B Luminescence Spectrometer.

F. Myosin Isozyme Distribution Pattern

Myosin was extracted and separated by gel electrophoresis under non-dissociating conditions and quantified and described earlier (Sen, S., and Young, D., *Hypertension* 8, pp. 918-924, 1986).

G. Effect of Myotrophin on Cell Size and Structure

The effect of myotrophin on cell size has been quantified using a Bioquant 4 image analysis system. The Bioquant system is comprised of a light microscope connected via a television camera to a Panasonic television monitor. The system is run on a host computer (IBM AT). A digitizer pad is used in conjunction with the computer system to allow morphometric analysis of projected images or printed micrographs. Neonatal myocardial cells are incubated with myotrophin or buffer for twelve hours and forty-eight hours, and the surface area is measured from projected images.

H. Fixation of Myocytes for Morphology

Both neonatal and adult myocytes are fixed by the addition of 2% glutaraldehyde in 0.1 M sodium cacodylate buffer, pH 7.4, for thirty minutes at 4° C. For scanning electron microscopy, 2% glutaraldehyde was used to fix the cells and dehydrated in ethanol and sputter coated on a 5-degree stage with gold platinum. For transmission electron microscopy, cell suspension was centrifuged at 55 g for fifteen minutes. The supernatant was removed and was replaced with cold glutaraldehyde for thirty minutes. The cell pellet was then diced into 1-mm cubes, fixed for another thirty minutes, washed the cacodylate buffer containing 7.5% sucrose, and postfixed for one hour at 40° C. in 1% osmium tetroxide in the same buffer. The tissue blocks were then dehydrated in ethanol, embedded in spurr resin, and then sectioned and stained with uranyl acetate before viewing with a Zeiss EM-10 transmission electron microscope (San Antonio, Tex., USA).

I. Statistical analysis

Statistical analysis was done by using the Student's t-test and by analysis of variance wherever appropriate. For bioassay in neonatal cells, data are analyzed from batches of neonatal cell experiments, each of which has two sets of controls (well #1 and well #6). The variable ratio of DPM/ng DNA is calculated for the second control relative to the first. For each cut point of percent stimulation, the proportion of samples where one control exceeds the other control's DPM/ng by that amount (% was calculated). The proportion was then divided by two to estimate the false positive rate. A confidence interval for the false positive rate was calculated based on the binomial distribution. Using a cut point of 25% stimulation, data showed the estimated proportion of false positive is 10% (95% interval from 3 to 22%). The estimated proportion of false positive using a cut point of 35%, the chances of false positive is 5% with a 95% confidence interval of 1 to 16%. In all assays for purification procedure, these guidelines have been followed.

RESULTS

1. Characterization of the Myocyte Assay System

Because of the variability of neonatal cells which have to be harvested anew for each assay, the inventors utilized several character schemes to establish the assay for the purposes of determining the effect of the factor. First, the inventors characterized the time course of amino acid incorporation into control cells. A linear rate of incorporation of $^3$H leucine occurred during one, two, and four hours of incubation into myocyte protein. On this basis, for routine assay, a two hour incubation time was used.

Second, the inventors characterized the myosin isozyme distribution patterns. The inventors found a normal isozyme distribution pattern for neonatal myocytes performed on three different batches of cells. Neonatal cells showed three types of myosin, namely $V_1$ (50.6%), $V_2$ (28.8%) and $V_3$ (20.6%). In the ventricles of 3- or 5-day old rat pups, the myosin isozymes are distributed in similar preparations of $V_1=50.6\%$, $V_2=20.4\%$, and $V_3=29\%$. Thus, neonatal cells, under the conditions used, consist of normal distribution of contractile elements, such as myosin, similar to cells of normal rats.

Third, the inventors looked at the effect of insulin on incorporation of $^3$H leucine into myocyte protein. Insulin in doses ranging from 0.25 to 1.0 μg was studied to determine the effect of insulin as an external standard. Shown in FIG. 1 are the data which is expressed as DPM/ng DNA. Each point represents a mean of at least 4 data points. The data indicates that insulin stimulated incorporation of $^3$H leucine into myocyte protein in a dose-dependent fashion from 0.25 μg to 1 μg ($P<0.01$).

Finally, the viability and integrity of the adult myocytes were defined by (a) examination under a phase contrast microscope, where a three dimensional, rod-shaped structure was found; and (b) the effect of the agonist, norepinephrine, directly and after pretreatment with the antagonist, propranolol, and counting the beating rate of the cells. A significant increase in beating rate was found after treatment with norepinephrine ($10^{-8}$ M), and this increase in beating rate could be prevented by the addition of propranolol. This result demonstrated the receptor integrity of these myocytes, which were maintained in culture for four days. The cells appeared cleanly separated at the lateral sarcolemmal borders and the intercalated discs. There was clear delineation of Z, I, and M bands. The myofilaments were well organized, and the mitochondria retained typical morphology with stacks of undisturbed christae.

Other features appeared to be well preserved and within normal ranges.

For the purposes of routine assays, insulin in a dose of 0.5 μg was used to serve as an external standard to assess proper function and viability of the myocytes prepared for each set of experiments. Experiments utilizing cells that did not respond to insulin were discarded.

2. Effect of Myocardial Homogenate on Neonatal Cells

Figure 2:
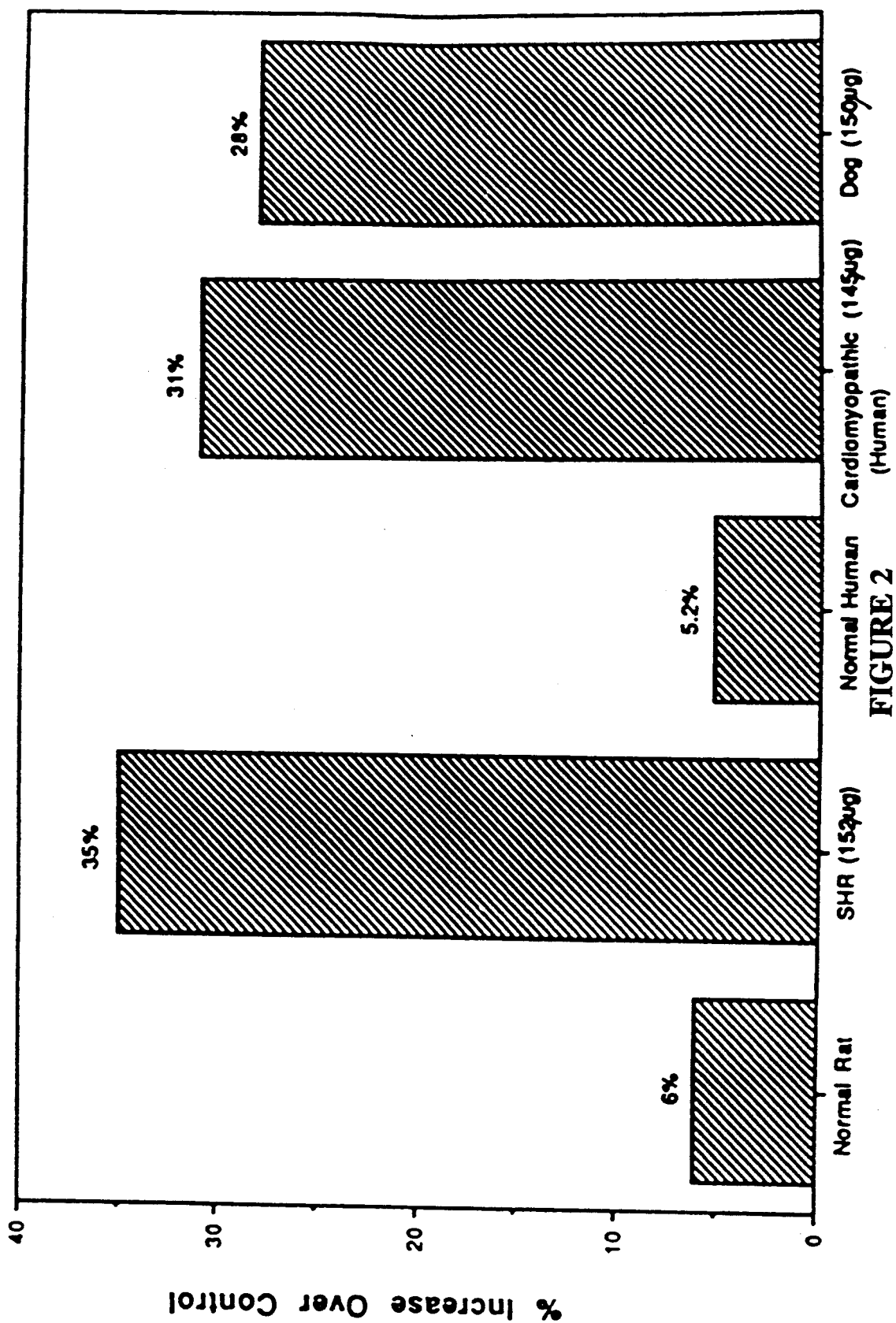
FIG. 2 is a graph indicating the effect of left ventricular homogenate (10,000 $\times$ g supernatant) on $^{14}$C phenylalanine incorporation into myocyte protein. Data are expressed as % increase over experimental control (cells only). The data shows that all three types of hypertrophied heart stimulated rate of incorporation and that the normal heart (both rat and human) did not stimulate incorporation significantly.

Three homogenates (10,000 ×g supernatant) from hypertrophied hearts of SHR, human cardiomyopathic heart and renal hypertensive dog heart, were prepared by the method described above. Normal WKY rat and normal human were also homogenized in the same manner. Approximately 145 μg of each was added to a neonatal assay system. A significant stimulation in the rate of incorporation was observed compared to normal rat (FIG. 2). This defined the existence of a factor in the hypertrophied SHR heart as well as other models of hypertrophied hearts, and served as a biological marker for the factor during the several steps of purification. In this example, the purification procedure for the stimulatory factor from SHR hearts only was discussed.

Figure 3A:
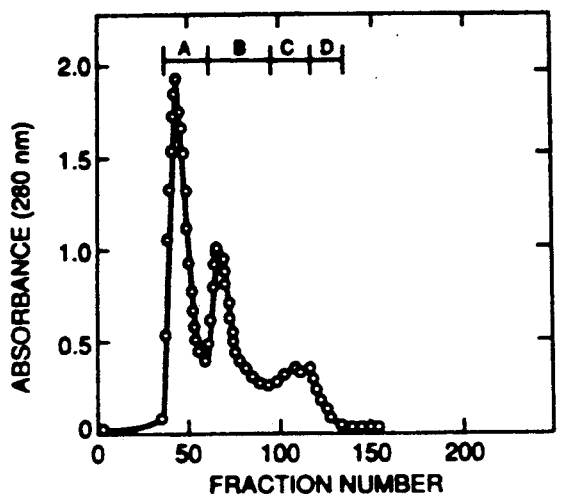
FIGS. 3A and 3B are graphs showing the G-75 Sephadex chromatogram of the myotrophin factor.
Figure 3B:
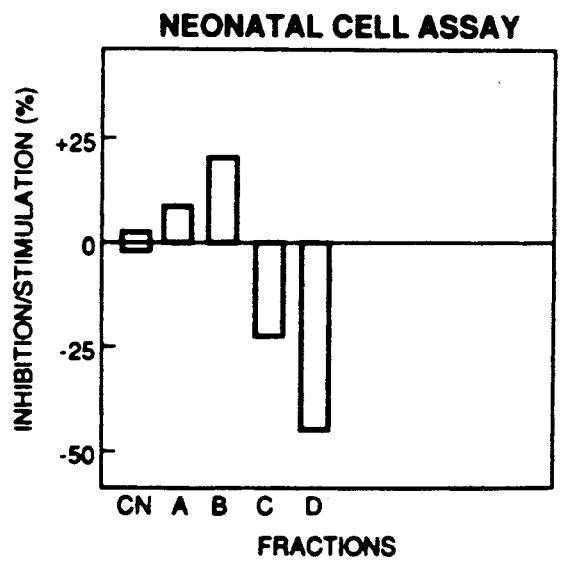
Figure 4A:
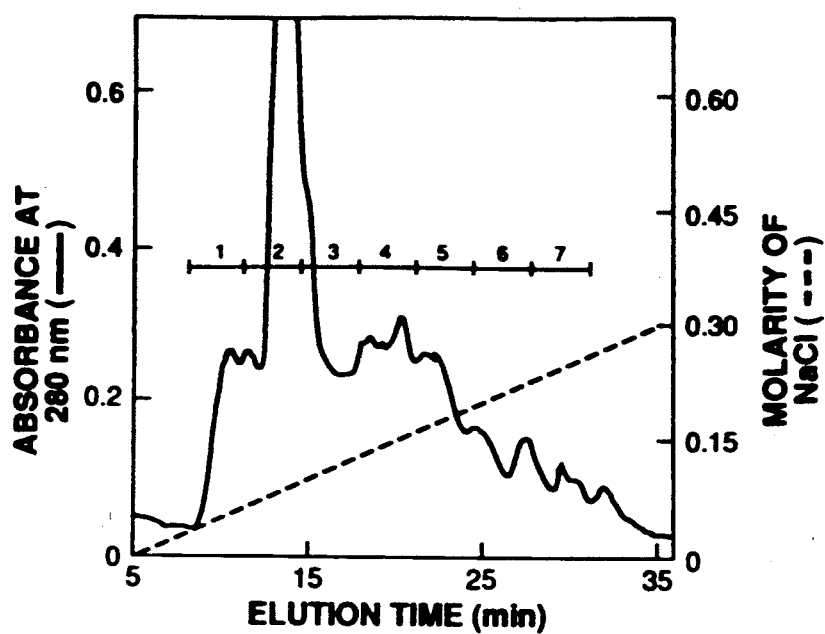
FIGS. 4A and 4B are graphs demonstrating a typical separation pattern of myotrophin by a FPLC first Mono-Q column.
Figure 4B:
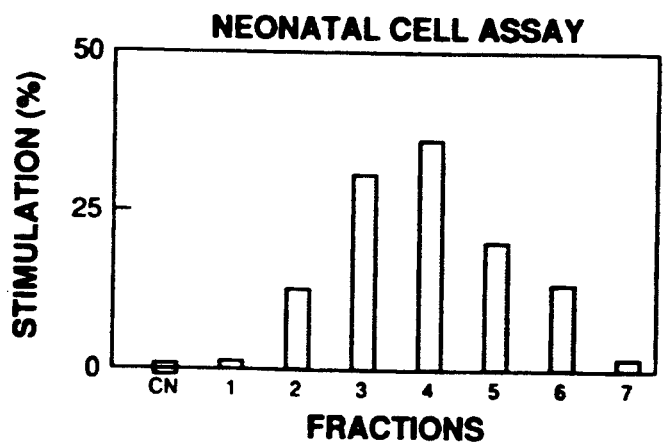

FIGS. 3A and 3B show the Sephadex G-75 chromatogram of the factor, of which peak "B" contained the stimulatory activity (FIG. 3B). Active fraction from Sephadex G-75 was pooled and applied to FPLC first Mono-Q column (See FIGS. 4A and 4B), and fraction 4 of this chromatogram showed the biological activity (FIG. 4B).

Figure 5A:
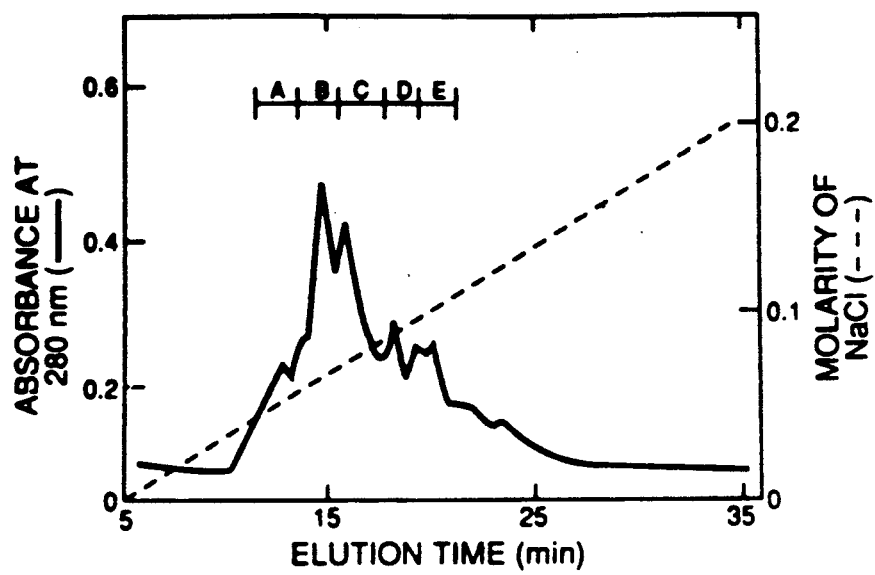
FIGS. 5A and 5B are graphs indicating a typical chromatogram of myotrophin by FPLC (Second Mono-Q-column).
Figure 5B:
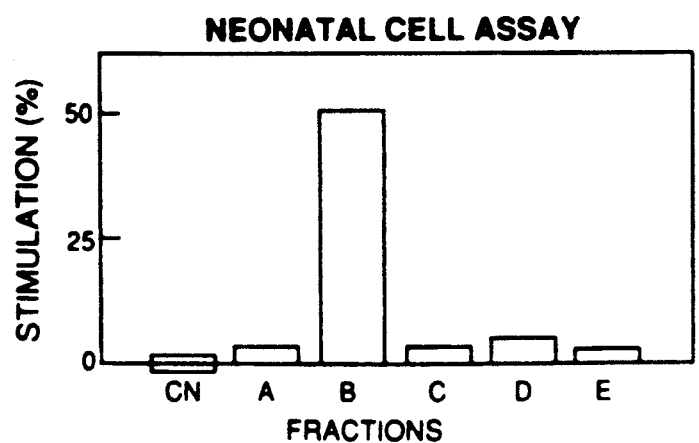
Figure 6A:
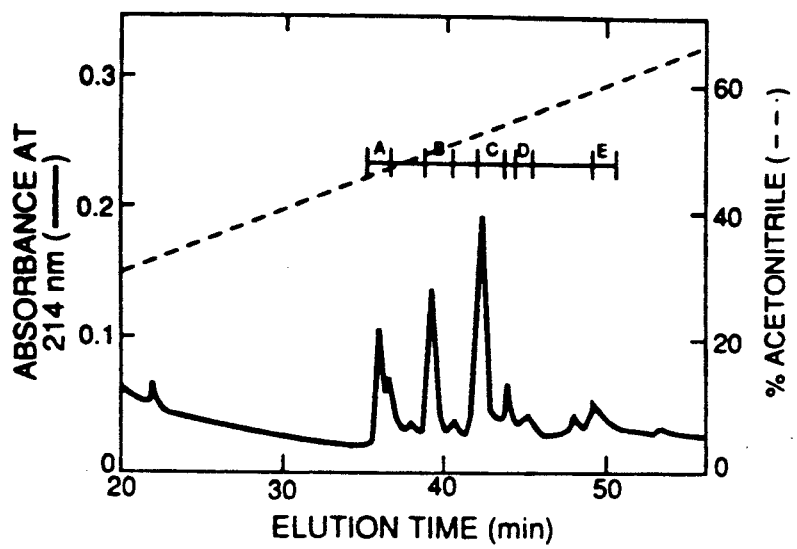
FIGS. 6A and 6B are graphs showing the typical chromatographic pattern of myotrophin by reverse-phase HPLC using Vydac $C_{18}$ column.
Figure 6B:
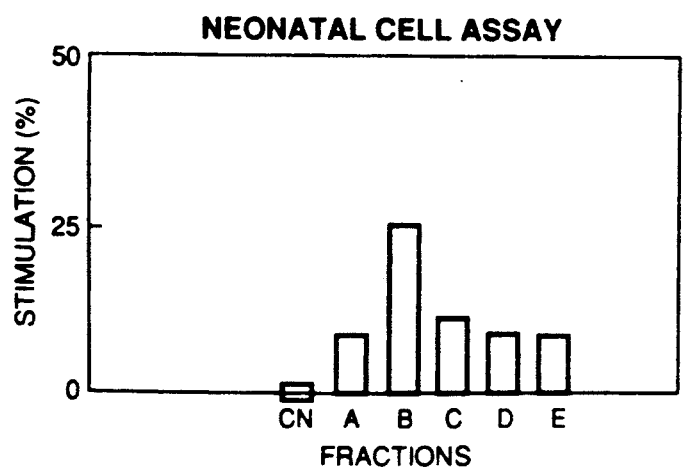
Figure 7A:
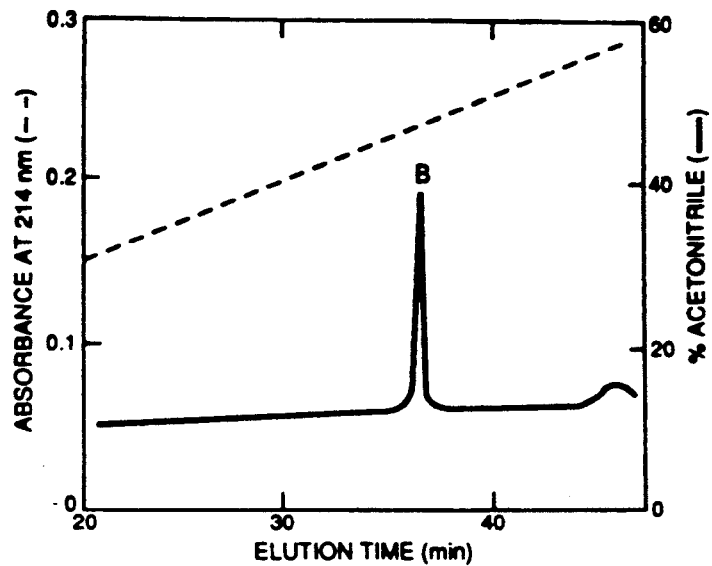
FIGS. 7A and 7B are graphs demonstrating the results of the final step of purification of myotrophin. Conditions used are the same as described under FIGS. 6A and 6B.
Figure 7B:
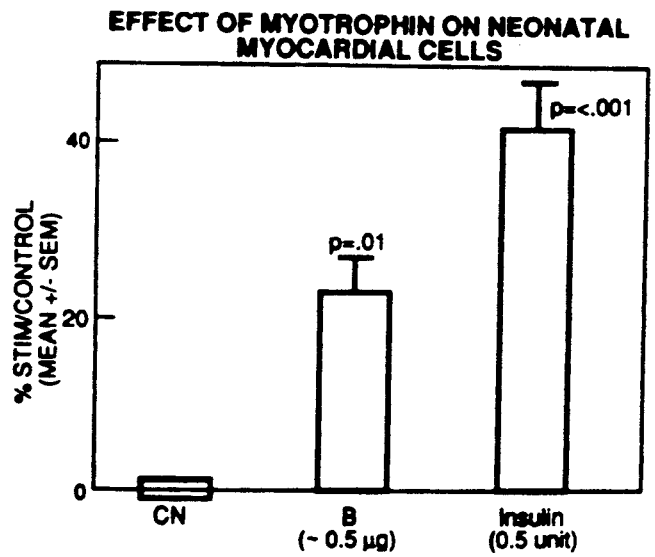

Active fraction from above was collected and applied again to the second Mono-Q column (see FIGS. 5A and 5B). Peak B contained the stimulatory activity (FIG. 5B). Further, the purification was achieved by HPLC using a Vydac $C_{18}$ column, and Peak B (FIGS. 6A and 6B) contained potent stimulatory activity. Finally, peak B was rechromatographed by HPLC under the same conditions as mentioned in FIG. 6 and showed potent stimulatory activation (See FIGS. 7A and 7B).

The biologically active fractions obtained from the neonatal cell assay system were re-assayed in the adult myocyte systems. The partially purified myotrophins (i.e. fraction B of the Sephadex G-75 Chromatogram), after gel filtration (8 μg), stimulated the rate of incorporation by 72%. The peak B of the FPLC second Mono-Q column showed a 54% stimulation. Insulin (1 μg) under similar conditions showed 24% stimulation. The data from the adult myocyte assay confirm the result obtained from neonatal cell assay.

Characterization of Myotrophin

Figure 8:
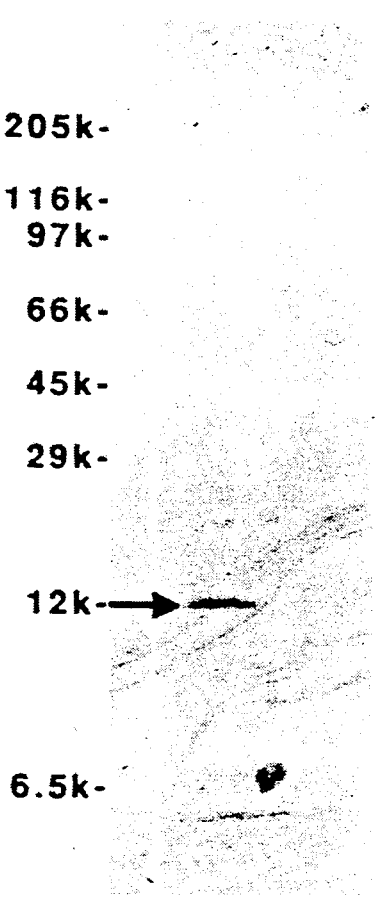
FIG. 8 is a photograph of the results of SDS polyacrylamide gel electrophoresis of pure myotrophin. The results indicate that the silver stain showed myotrophin migrated as a single band in the area of Mr 12,000 daltons.

SDS gel electrophoresis of purified myotrophin followed by silver staining gave a single band at the position corresponding to an apparent $M_r$ of 12,000 Da (FIG. 8). This observation further confirmed the homogeneity of myotrophin.

Furthermore, as indicated above, directed Edman degradation of intact myotrophin failed to yield any detectable PTH amino acids, indicating that the $NH_2$ terminus was blocked.

Figure 9:
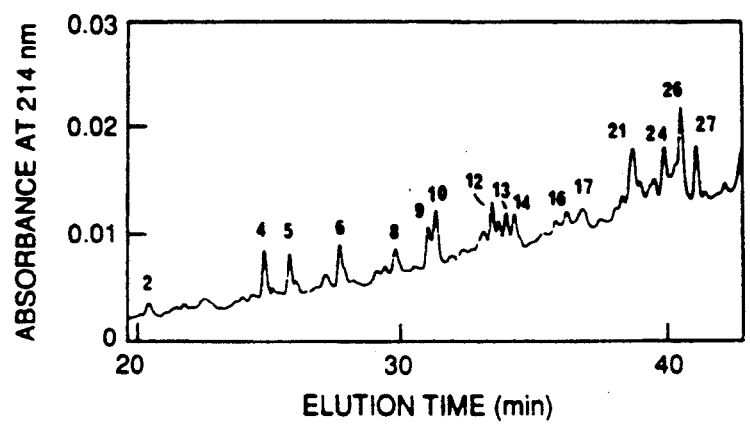
FIG. 9 is a graph illustrating the separation of tryptic fragments of nyotrophin by reverse phase HPLC on a Vydac $C_{18}$ column.

In order to obtain an internal sequence of myotrophin, the purified protein was reduced, carboxymethylated, and then digested with TLCK-treated trypsin. The digested material was separated by reverse phase HPLC (FIG. 9), where at least 24 tryptic peptides were obtained. Edman degradation of the materials under the peas 4, 9, 10, 27, 13, and 6 yielded 7, 7, 23, 17, 5, and 27 amino acid residue sequences, which are shown in Table 1 below.

TABLE 1

A Partial Amino Acid Sequence of Myotrophin

1. V Y V D A T K
2. Y G G F M E V
3. A D I T V I G P D G L T A L E A T D N E A I D (H)
4. L L L S I G A D I T V X G P X E V
5. Y G G F K
6. G A D K T V K G P (C) G L T A L A S I N Q A I (X) A L L

X = not definite

A sequence of homology search was carried out on the Protein Identification Resources (that contains 6,330 entries) and Swiss-Prot protein sequence databases (that contains 10,008 entries). None of the sequences in the above databases contained segments identical to any of the test segments of myotrophin. After initial screening using PROTSCAN computer program (Lipman, D. J., and Pearson, W. M., Science 227, p. 1435, 1985), the sequence alignment score was calculated by the method of Lipman and Pearson (Lipman, D. J., and Pearson, W. M., Science 227, p. 1435, 1985) using the Fast P Scan program. No sequence with the number of standard deviations greater than 10 was found (see Table 2 below) concerning the four fragment sequences 17, 2, 7, and 7 amino acid residues. This showed that mytrophin is a novel peptide, and its internal sequence has not been reported before.

TABLE 2

| Search Statistics of Protein Sequences | | | |
|---|---|---|---|
| | No. of Comparison | Mean of All Scores | Standard Scores |
| 17-A-A Residue | 13413 | 0.20 | 0.52 |
| 2-A-A Residue | 13413 | 0.02 | 0.15 |
| 7-A-A Residue | 13413 | 0.01 | 0.11 |
| 7-A-A Residue | 13413 | 0.01 | 0.11 |

Figure 10:
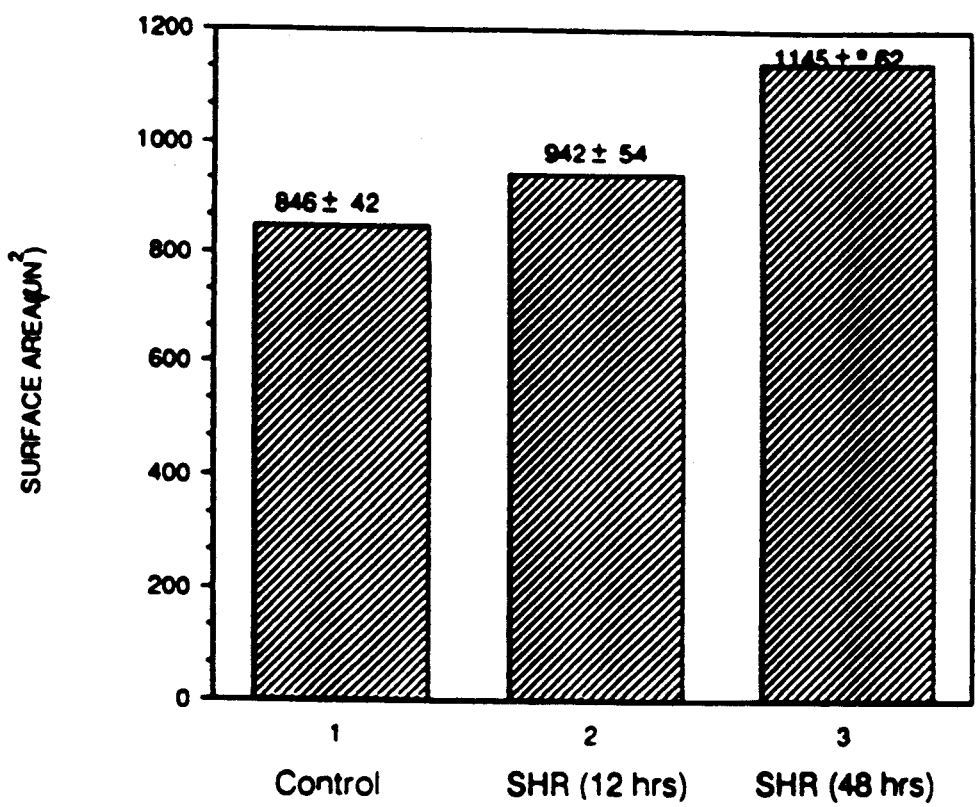
FIG. 10 is a graph demonstrating the effect of myotrophin on cell surface area as quantified by bioquant technique. Note that the treatment of neonatal cells for 48 hours showed a significant increase in cell surface area compared to vehicle treated control cells.

Search Parameters:
K - tuple value - 2
# of Diagonal Savings - 6
Threshold for Savings - 4.5 standard deviation
Scoring Policy: Sum of subalignment exceeding threshold Effect of Myotrophin on Cell Size The effect of myotrophin on cell size is shown in FIG. 10. When myotrophin was added to neonatal myocardial cells, it increased the cell size in a time-dependent fashion. The data showed that myotrophin from SHR ventricles increases the cell surface area of myocytes (FIG. 10). In a separate experiment, myotrophin was added to other cells, and it did not demonstrate any measurable effect on cell size of fibroblast, endothelial cell or aortic smooth muscle cell sizes.

Effect of Myotrophin on Cell Morphology

Figure 11:
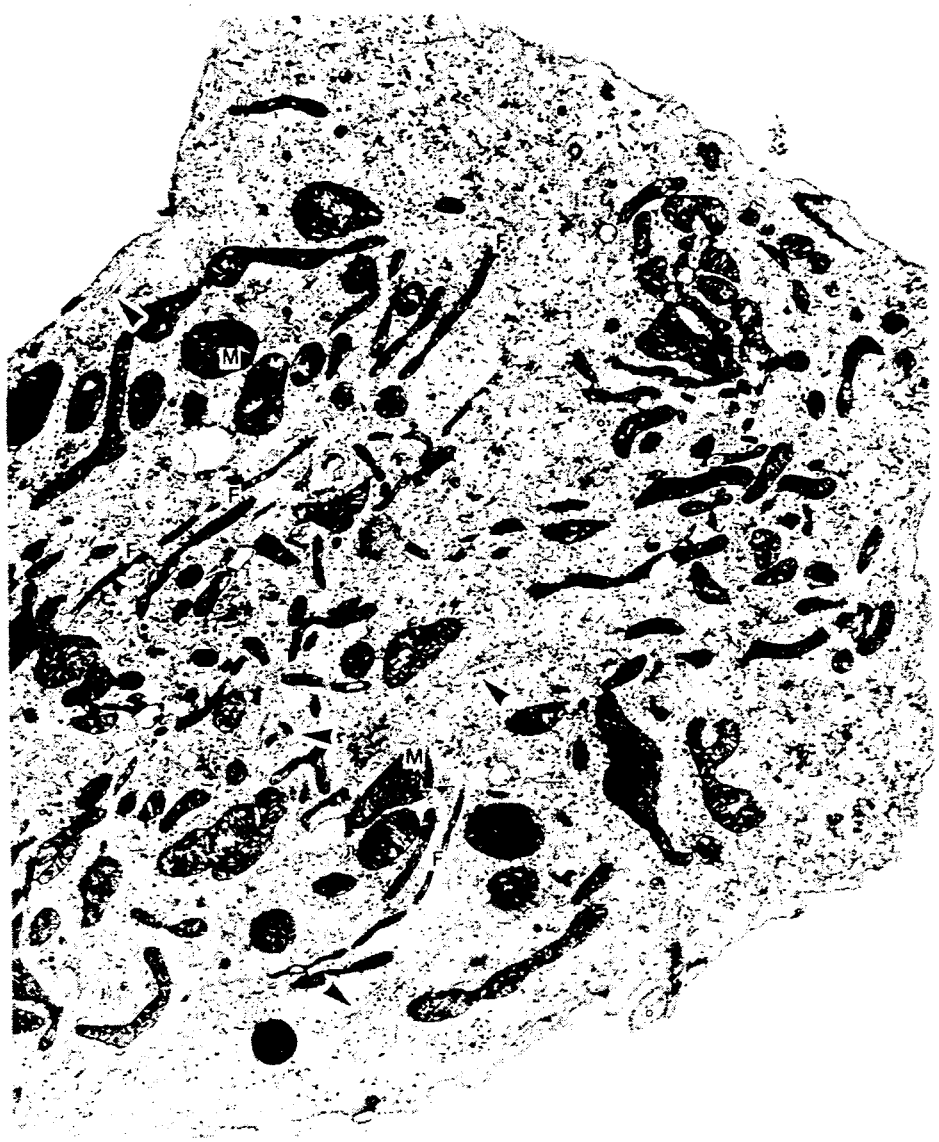
FIG. 11 is an electronmicrograph of controlled neonatal rat cardiomyocytes myocytes in culture ($\times$5000). The results indicate that the control myocytes showed normal healthy mitochondria and nuclei and few myofibrils. The cells maintained in culture appeared to be healthy and normal.
Figure 12:
FIG. 12 is an electronmicrograph of neonatal rat cardiomyocytes cells ($\times$5000) treated with myotrophin (pure) in a dosage of 0.4 $\mu$/24 hour for 48 hours. The results indicate the appearance of well organized myobril, healthy nuclei and mitochondria, demonstrating the accelerated growth and differentiation of myocardial cells due to myotrophin treatment.

The effect of myotrophin on neonatal cells at EM level is shown in FIGS. 11 and 12. Myotrophin demonstrated a considerably accelerated myofibrillar growth and organization as well as maturation of mitochondria of neonatal cells. This significant myofibrillar growth was observed in neonatal cells treated with myotrophin, both for twelve and twenty four hours. In three different sets of experiments, ten sections obtained from various areas of control cells showed only scattered myofibrils in the periphery or scattered in the cytoplasm. The twelve hour myotrophin-treated cells showed further organization of myofibril as documented by 9 out of 16 sections showing accelerated growth. In 24-hour treated cells, the maturity was further enhanced, as documented by 12 out of 22 sections showing a considerable amount of myofibril in the cells occupying close to 50% of the area of the cytoplasm. Compared with the control, both twelve and twenty four hour, myotrophin treated cells showed considerable acceleration in growth.

DISCUSSION

The inventors previously reported (Sen, S. and Petscher, C., *Hypertension* 9, pp. 261-266, 1987; and, Sen, S., *Circulation* 75, pp. 181-184, 1987) the existence of a factor in the hypertrophied myocardium of SHR that may stimulate protein synthesis in adult myocytes. In addition, the inventors described the partial purification of this factor and demonstrated its effect, i.e. the increased incorporation of $^{14}C$ phenylalanine, on myocytes protein. More importantly, the inventors showed that the specific activity of leucyl tRNA was increased without a significant change in the intracellular leucine pool. Furthermore, the absolute rate of protein synthesis was increased from $4.02 \pm 0.30$ in control cells to $7.0 \pm 0.20$ pmol leucine/ g protein/h ($P < 0.005$) (Sen, S. and Petscher, C., *Hypertension* 9, pp. 261-266, 1987). In addition, the inventors also demonstrated that trypsin digestion (pH 7-7.5) destroyed the stimulatory activity. All of this information together suggested that the factor the inventors discovered is a protein.

In the investigation which resulted in the present invention, the inventors have completed the purification of this protein molecule, established its homogeneity by three different criteria, and partially sequenced it. This is a significant advancement over applicants' previous studies in that this is the first time the protein factor has been completely purified to its apparent homogeneity as well as partially characterized. Moreover, the investigation which lead to the present invention, clearly demonstrates that this protein factor is a novel peptide that stimulates myocyte growth in a manner not reported previously. In addition, the investigation showed that the protein further has a significant effect on the cell surface area and morphology, demonstrating its pathophysiological significance.

More particularly, in the investigation which resulted in the present invention, the inventors demonstrated the existence of a peptide derived from hypertrophied SHR hearts protein that stimulates protein synthesis in vitro in both neonatal and adult myocytes maintained in culture. The inventors further purified the protein factor (molecular wt. 12,000 Da) to homogeneity and elucidated a partial amino acid sequence. From a homology search using three databases, it appears to be a novel molecule with no identical homology with any known protein. The inventors believe the factor is unique, and have therefore named it "myotrophin". In addition, the inventors have shown that myotrophin enlarges cell surface area and, qualitatively in an associated pilot study, demonstrated that myotrophin enhances maturation of myocardial cells.

The identification of the myotrophin peptide was made possible by the definition of a quantifiable biological effect of the factor on myocytes in cell culture. Along this line, the linear incorporation of $^3H$ leucine into myocyte protein during a four hour incubation time was found, along with the effect of externally added insulin, as a standard for cell uniformity and viability from day to day (0.5 µg). The cell culture systems utilized were similar to what has been reported by Claycomb (Claycomb, W. C., *Exp. Cell Res.* 131, pp. 231-236, 1980) and Bugaisky and Zak (Bugaisky, L. B. and Zak, R., *Circ. Res.* 64, pp. 493-500, 1989). In addition, in the inventors' system, at the end of the experiments, the inventors added SDS-NAOH to completely lyse the cells to measure the DNA content to express the data as DPM/µg DNA. The inventors have also introduced statistical analysis to exclude false positive data for stimulation (See the statistical analysis discussed above).

In this regard, Claycomb (Claycomb, W. C., *Exp. Cell Res.* 131, pp. 231-236, 1980) demonstrated that a neonatal cell system can be used to study the effect of an exogenous factor on cell growth in the absence of transferrin and fetuin, which he recommended to be removed on the day of the assay. Claycomb demonstrated that even removal of transferrin and fetuin on the third day did not interfere with the health of the cell or its differentiating morphology. In the example described above, the inventors used a method similar to that described by Claycomb (Claycomb, W. C., *Exp. Cell Res.* 131, pp. 231-236, 1980), and the results agree with Claycomb's conclusion that cells grown in serum-free media can be used as an assay system to study the effect of an exogenous factor on cell growth.

In addition, in the example set forth above, the inventors used two assay systems, neonatal and adult myocyte, to evaluate the effect the protein factor had on all growth. The reason for using two types of systems is that the responsiveness of adult and neonatal cells to growth factor(s) may be quite different. Along this line, Simpson, et al. (Simpson, P., McGrath, A., Savion, S., *Circ. Res.* 51, pp. 787-801, 1982) showed that norepinephrine stimulated growth in neonatal cells, however, norepinephrine had no effect on growth of adult myocytes (Hammond, G. L., Weiben, E., and Market, C. L., *Proc. Natl. Acad. Sci. (USA)* 76, pp. 2455-2458, 1979). However, the present inventors have discussed that myotrophin stimulated protein synthesis in both neonatal and adult myocytes.

Furthermore, the assay system used to define a trophic effect on the heart is a major methodologic challenge. Evidence for the existence of a soluble factor that enhances myocardial protein synthesis has also been reported by Hammond, et al. (Hammond, G. L., Weiben, E., and Market, C. L., *Proc. Natl. Acad. Sci. (USA)* 76, pp. 2455-2458, 1979) using an intact heart model system. Hammond, et al. also showed that the homogenate from a hypertrophied dog heart, due to banding of the aorta, stimulated protein synthesis in an Langendolf heart preparation. Although, Hammond, et al. failed to purify this factor to demonstrate its nature or physiological significance, their studies also suggested that the homogenate from hypertrophied hearts that stimulated protein synthesis was not species-specific (Hammond, G. L., Lai, Y. K., and Market, C. L., *Science* 216, pp. 529-531, 1982).

The inventors' discoveries indicated above also suggest this observation, as myotrophin obtained from hypertrophied human heart or dog heart stimulated protein synthesis in rat myocytes. However, Hammond, et al. failed to purify their factor to demonstrate its nature or physiological significance. Furthermore, the methodologic limitations of an intact beating heart assay system utilized by Hammond, et al. are not substantial, particularly since it is not clear which cells in the myocardium are responsible for increased protein synthesis, or if DNA synthesis is also increased. The present inventors have demonstrated the existence of a stimulating factor somewhat similar to that disclosed by Hammond, et al. in the homogenate from hypertrophied rat heart. In addition, the inventors have completed the purification of the stimulating factor, demonstrated its homogeneity, elucidated its structure, and have demonstrated the physiological significance of this factor, as evidenced by an increase in cell size and accelerated myofibril growth.

In addition, with the advancement and availability of more refined cell and molecular biological techniques, several studies have reported the possible existence of signal proteins during cardiac overload. Moalic and Swynghedauw (Moalic, J. M. and Swynghedauw, B., *J. Mol. Cell Cardiol* (*Suppl.* 4) 19, p. S30, 1987) demonstrated that during the transition that precedes the compensatory hypertrophy, two distinctive, reproducible spots appear on the gel electrophoresis that may correspond to signal proteins for protein synthesis. Furthermore, these investigators have demonstrated that thirty days after banding, a reproducible observation was the appearance of beta tropomyosin, an isoform normally absent in the left ventricle, which characterizes slow skeletal muscles. Using a bioassay system similar to that of the present inventors, Mann and Cooper (Mann, D., and Cooper, G., *J. Mol. Cell Cardiol.* 19, p. S260, 1987) demonstrated that, when freshly isolated myocytes are maintained in culture in a serum-free medium for three days, in one group of cardiocytes, diastolic resting length increased 10% by stretching the substance to which cells adhered. In a second experimental group, cells were continuously exposed to 1.0 mM norepinephrine. On the third day, the cells were pulse labeled with $^3$H leucine or $^{14}$C phenylalanine to assay protein synthesis. The cells that were stretched showed an increase in protein synthesis, whereas those exposed to norepinephrine showed a reduction in protein synthetic activity. They concluded from their in vitro system that load, not adrenergic receptor activation, was responsible for increased RNA and protein labeling, and likely therefore in the initiation of growth and hypertrophy in adult cardiocytes.

Recently, Havre and Hammond (Havre, P. A. and Hammond, G. L., *J. Mol. Cell Cardiol.* (*Suppl.* 4) 19, p. S30, 1987) examined the effect of translational activity of protein extract substance from control dog heart and acute hearts stressed by aortic banding and heat shock, using an in vitro translational assay. They demonstrated that the extract from stressed tissue exhibited approximately 50% greater suppressive activity than extract obtained from control tissue. Havre and Hammond have purified the factor and named it "TIP".

Furthermore, fairly recently, Henrich and Simpson (Henrich, C. and Simpson, P. C., *Circulation* 80, pp. II-451, 1989) reported the existence of a heparin-binding hypertrophic growth factor(s) for cardiac myocytes. The specific nature of this factor appeared to be different from the known peptide growth factors. The specific nature, however, is yet to be defined.

As a result, it is clear that many factors lead to the growth of terminally differentiated myocytes. It is likely that one or more chemical signals ultimately translate the variety of mechanical and humoral stimuli into the message for cell growth, or cell atrophy. The factor that the inventors describe here appears to be a novel peptide which has the effect of stimulating the myocyte to grow but not to divide, suggesting that this factor plays a role in cell differentiation and hypertrophy.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. The partial amino acid sequence of myotrophin selected from the group consisting of:
V Y V D A T K;
Y G G F M E V;
A D I T V I G P D G L T A L E A T D N E A I D (H);
L L L S I G A D I T V X G P X E V;
Y G G F K; and,
G A D K T V K G P (C) G L T A L A S I N Q A I (X) A L L,
wherein the partial amino acid sequence of is myotrophin determined by a process comprising the steps of:
   a) providing myotrophin which has been purified to homogeneity;
   b) reducing the purified myotrophin with dithiothreitol in a quanidine-HCL containing Tris-HCL buffer;
   c) carboxymethylating the reduced myotrophin by adding iodoacetic acid to the reduced solution;
   d) digesting the carboxymethylated myotrophin by adding trypsin to the carboxymethylated mixture;
   e) separating the digested material by reverse phase HPLC; and,
   f) sequencing the separated material.

* * * * *